(12) United States Patent
Vadera

(10) Patent No.: US 9,936,883 B2
(45) Date of Patent: Apr. 10, 2018

(54) TEMPORARY OR LONG TERM IMPLANTATION DEVICE FOR INTRACRANIAL PROBES HAVING HEMATOMA DETECTION APPARATUS, AND METHOD OF USING DEVICE THEREOF

(71) Applicant: Sumeet Vadera, Irvine, CA (US)

(72) Inventor: Sumeet Vadera, Irvine, CA (US)

( * ) Notice: Subject to any disclaimer, the term of this patent is extended or adjusted under 35 U.S.C. 154(b) by 354 days.

(21) Appl. No.: 14/805,258

(22) Filed: Jul. 21, 2015

(65) Prior Publication Data

US 2016/0113519 A1     Apr. 28, 2016

Related U.S. Application Data

(60) Provisional application No. 62/027,174, filed on Jul. 21, 2014.

(51) Int. Cl.
*A61B 5/02*     (2006.01)
*A61B 10/02*     (2006.01)

(52) U.S. Cl.
CPC ...... *A61B 5/02042* (2013.01); *A61B 10/0233* (2013.01); *A61B 2505/05* (2013.01)

(58) Field of Classification Search
CPC ................. A61B 10/0233; A61B 5/02042
See application file for complete search history.

(56) References Cited

U.S. PATENT DOCUMENTS

| 7,850,664 B1 * | 12/2010 | Pruter | A61B 46/10 600/562 |
| 2010/0111763 A1 * | 5/2010 | Kahn | A61B 5/02042 422/400 |

\* cited by examiner

*Primary Examiner* — Puya Agahi

(57) ABSTRACT

A biopsy needle surrounded by a peel away sheath chemically impregnated with a blood detection composition enabling a user (e.g., a surgeon) to accurately and timely determine the existence of a blood pooling or hematoma when passing an implantable (e.g., deep brain stimulation probes) or non-implantable (e.g., biopsy needle) device into a region of the subject's body (e.g., a brain) to gather tissue for further analysis. A biopsy needle may be provided wherein the needle is tightly surrounded by a peel-away sheath that is chemically impregnated with a blood detection composition. The surgeon may insert the biopsy needle into the subject and peel away the chemically impregnated sheath in order to assess whether or not a blood pooling or hematoma exists, and act immediately to address the blood pooling or hematoma.

2 Claims, 6 Drawing Sheets

TEMPORARY OR LONG TERM IMPLANTATION DEVICE FOR INTRACRANIAL PROBES HAVING HEMATOMA DETECTION APPARATUS, AND METHOD OF USING DEVICE THEREOF

CROSS-REFERENCE TO RELATED APPLICATIONS

This application claims the priority benefit of U.S. Provisional Patent Application No. 62/027,174, filed on Jul. 21, 2014, the disclosure of which is incorporated herein by reference in its entirety.

BACKGROUND

1. Field

Example embodiments of the present disclosure relate to a temporary or long term implantation device for intracranial probes having a hematoma detection apparatus, which serves to instantly notify a surgeon of the existence of hematoma during any invasive probe placement into the brain. The temporary or long term implantation devices include, but are not limited to, deep brain stimulation, intracranial electrodes for epilepsy monitoring, external ventricular drain placement, and needle biopsy.

2. Description of Related Art

When an abnormality of the brain is suspected, a brain biopsy is often performed to obtain a sample of brain tissue for further testing and/or analysis. For instance, a stereotactic brain needle biopsy is performed by probing the brain tissue in three dimensions. Generally, during the biopsy procedure, the biopsy needle is guided on a path determined by a computer system, for example, a CT or MRI scan. However, during the brain biopsy procedure, a problem may arise when the biopsy needle causes a hematoma in the brain. In this case, immediate attention should be given to the hematoma to avoid damage to the brain.

Accordingly, there exists a need for accurately and timely detection of blood pooling during a brain biopsy procedure, and for providing instant visually notification to the surgeon of the existence of hematoma during the biopsy procedure so that immediate corrective action may be taken.

SUMMARY

The various embodiments of the following disclosure are provided in order to solve the above-described problems. For instance, a user (e.g., a surgeon) may accurately and timely determine the existence of a blood pooling or hematoma when passing an implantable or non-implantable device (including but not limited to deep brain stimulation, intracranial electrodes for epilepsy monitoring, external ventricular drain placement, and needle biopsy) into a region of the subject's body for intracranial probing.

According to an example embodiment of the present disclosure, an exemplary biopsy needle is provided wherein the needle is tightly surrounded by a peel-away sheath that is chemically impregnated with a blood detection composition. The surgeon may insert the biopsy needle into the subject and peel away the chemically impregnated sheath in order to assess whether or not a blood pooling or hematoma exists, and act immediately to address the blood pooling or hematoma. Although the following disclosure is mainly directed to a peel away sheath surrounding a biopsy needle, the present disclosure is not limited thereto. That is, the chemically impregnated peel away sheath may tightly surround other devices not described herein.

According to another example embodiment, an implantation device for brain biopsy needles is provided, the implantation device including: a sheath surrounding a barrel of a brain biopsy needle, the sheath contacting the barrel and having a tubular shape with at least one perforation along an axial direction of the sheath; and at least two grip protrusions attached to an upper portion of the sheath, such that an external force applied to the at least two grip protrusions initiates a tearing of the at least one perforation along the axial direction of the sheath, wherein the sheath comprises a film that is chemically impregnated, such that when the film makes contact with blood, an observable property of the film changes providing an indicator that the blood has been detected, and wherein when the external force is applied to the at least two grip protrusions over a period of time, the at least one perforation along the axial direction of the sheath tears, such that the tubular shape of the sheath is divided.

According to yet another example embodiment, a method for detecting hematoma during a brain biopsy is provided, the method including: providing a chemically-impregnated sheath surrounding a barrel of a brain biopsy needle, the chemically-impregnated sheath having at least two protrusions disposed at an upper portion; inserting the barrel of the brain biopsy needle together with the chemically-impregnated sheath into the brain; applying an external force to the at least two protrusions, while the barrel of the brain biopsy needle remains inserted into the brain, such that the external force tears the chemically-impregnated sheath into two portions, separates the chemically-impregnated sheath from the barrel, and extracts the two portions of the sheath from the brain; and providing a blood-detection indicator indicating that the chemically-impregnated sheath detected blood while the chemically-impregnated sheath was inserted into the brain.

BRIEF DESCRIPTION OF DRAWINGS

A better understanding of the present disclosure may be obtained upon reference to the following drawings together with the following detailed description thereof, wherein like reference characters refer to like parts throughout the various illustrations.

DETAILED DESCRIPTION

Figure 1:
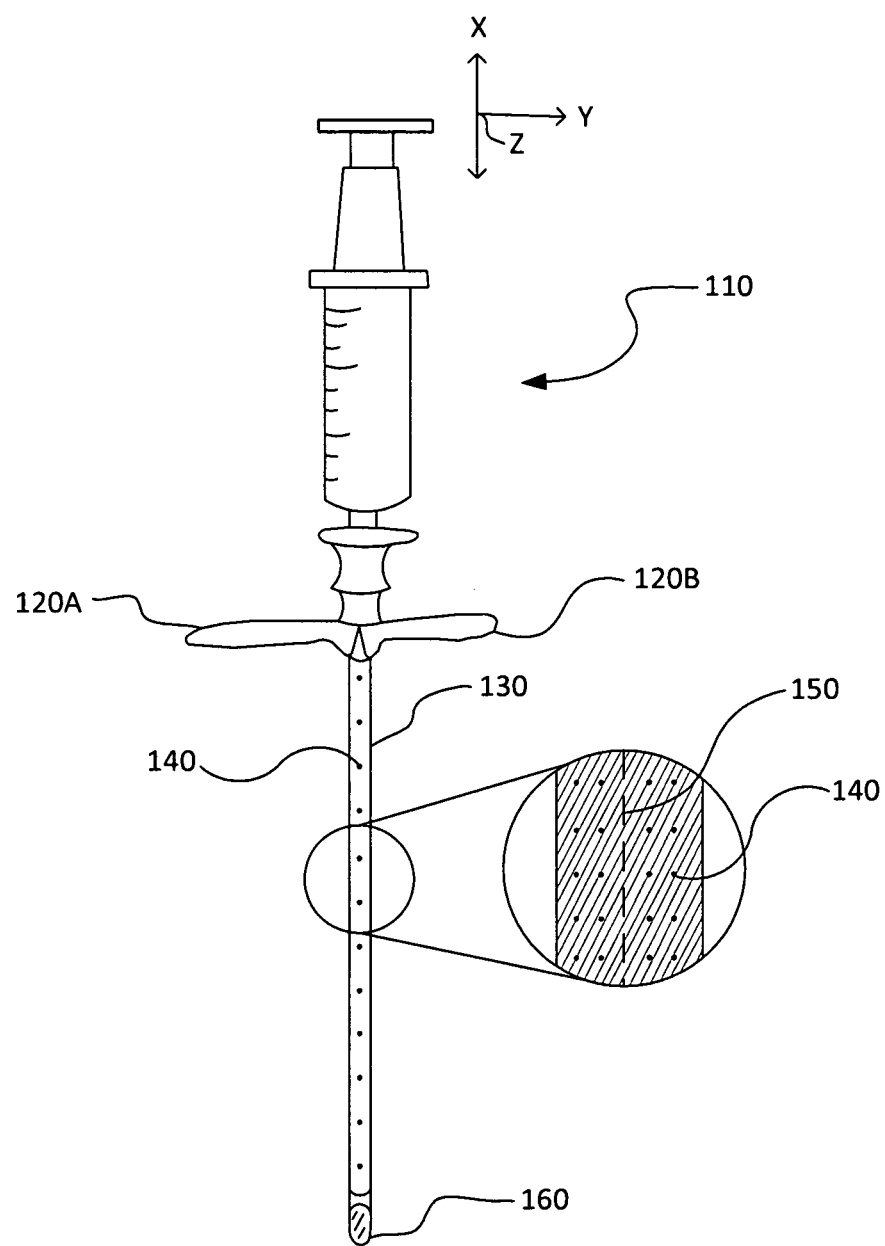
FIG. 1 is a perspective view of a biopsy needle surrounded by a peel-away sheath impregnated with a blood detection composition, according to an example embodiment of the present disclosure.
Figure 2:
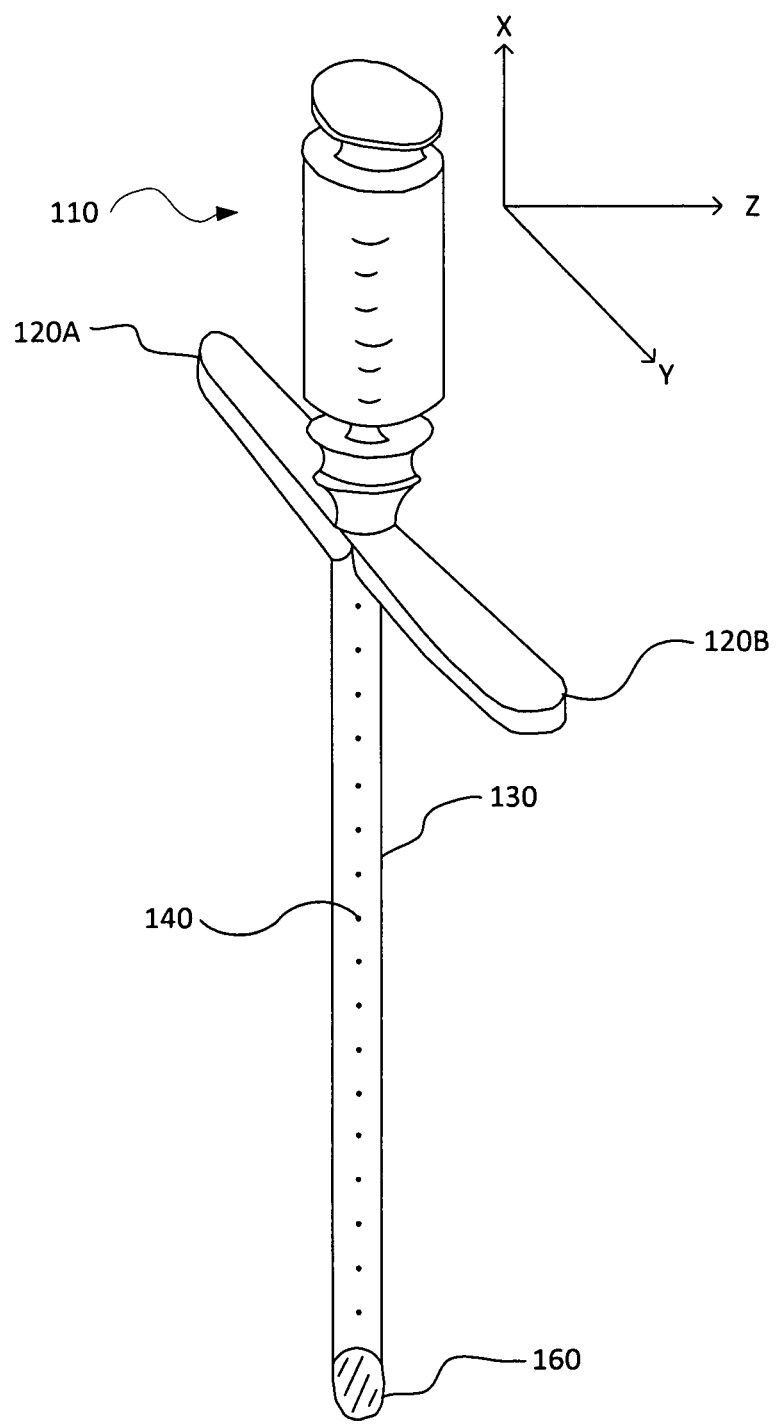
FIG. 2 is another perspective view of a biopsy needle surrounded by a peel-away sheath impregnated with a blood detection composition, according to an example embodiment of the present disclosure.

FIGS. 1-2 are views of a biopsy needle surrounded by a peel away sheath impregnated with a blood detection composition from different perspectives, according to an example embodiment of the present disclosure.

Referring to FIG. 1, a biopsy needle surrounded by a peel-away sheath, according to example embodiments of the present disclosure, is illustrated. A biopsy needle system 100 may include at least a syringe 110, a left grip fingerhold 120a, a right grip fingerhold 120b, a barrel 130 having a beveled edge 160, and a peel-away sheath 140. The biopsy needle system 100 is not limited to the above elements, and may selectively include additional or fewer elements.

In the biopsy needle system 100, the barrel 130 may be tightly surrounded by the peel-away sheath 140, such that the peel-away sheath 140 may slide upwards or downwards along the outer surface of the barrel 130. In an example embodiment, the peel-away sheath 140 is a single-use disposable plastic film that is manufactured as one plastic film having two lines of perforations for easy removing. After blood detection is performed, the peel-away sheath 140 may be discarded once the peel-away sheath 140 is peeled into a left portion and a right portion.

Depending on example embodiments, the peel-away sheath 140 may include two sets of perforations 150 located down the peel-away sheath 140 in an axial direction (as shown in FIG. 1). Further, the peel-away sheath 140 may be connected to the left grip fingerhold 120a and the right grip fingerhold 120b.

According to an example embodiment, the peel-away sheath 140 may be chemically impregnated with a blood detection composition. As only a non-limiting example, the peel-away sheath 140 may be composed of a plastic film in which a testing reagent is impregnated, disposed, or provided. The peel-away sheath 140 including the plastic film being chemically impregnated with a testing reagent may provide a visual signal or indication upon contact with blood. For example, a color may change to a predetermined color upon contact with blood, thereby visually indicating to a user that blood has been detected. The testing reagent impregnated into the plastic film may include gum guaiac, or other derivatives naturally or artificially occurring thereof, which indicate the presence of blood. The above described impregnation of a plastic film using gum guaiac is exemplary, and thus, the present disclosure is not limited thereto. That is, other testing reagents which indicate the presence of blood, and which may be impregnated into a plastic film, may be used as the peel-away sheath 140 surrounding the barrel 130. In other embodiments, the peel-away sheath 140 may be entirely composed of a material capable of providing a visual indication of blood detection, instead of including a chemically-impregnated plastic film.

In yet another embodiment, the peel-away sheath 140 may detect bacterial proteins instead of a hematoma or blood. That is, for example, when an implantable device is used, the plastic film of the peel-away sheath may be chemically impregnated with a composition, such that the plastic film shows color changes upon interaction with bacterial protein.

Figure 3A:
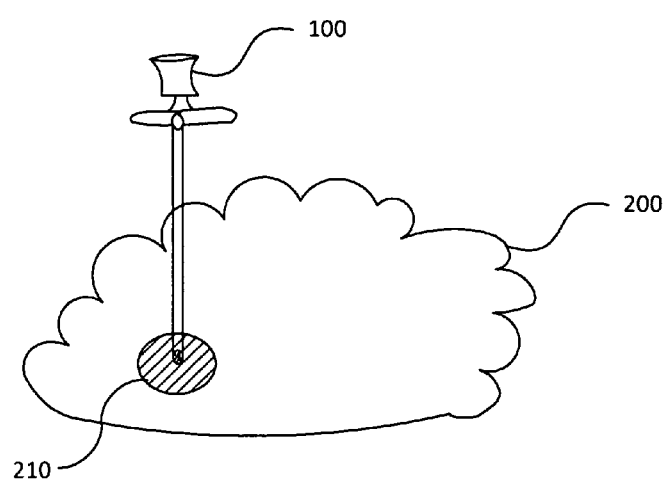
FIGS. 3A-3C illustrate the biopsy needle surrounded by a peel away sheath in use during a biopsy procedure, according to an example embodiment of the present disclosure.
Figure 3B:
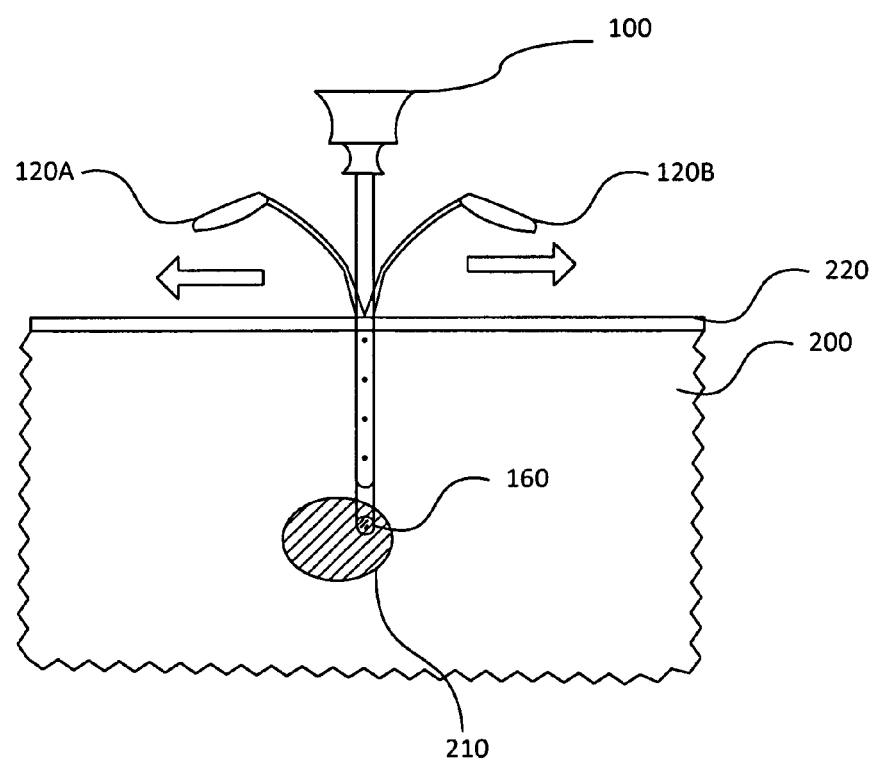
Figure 3C:
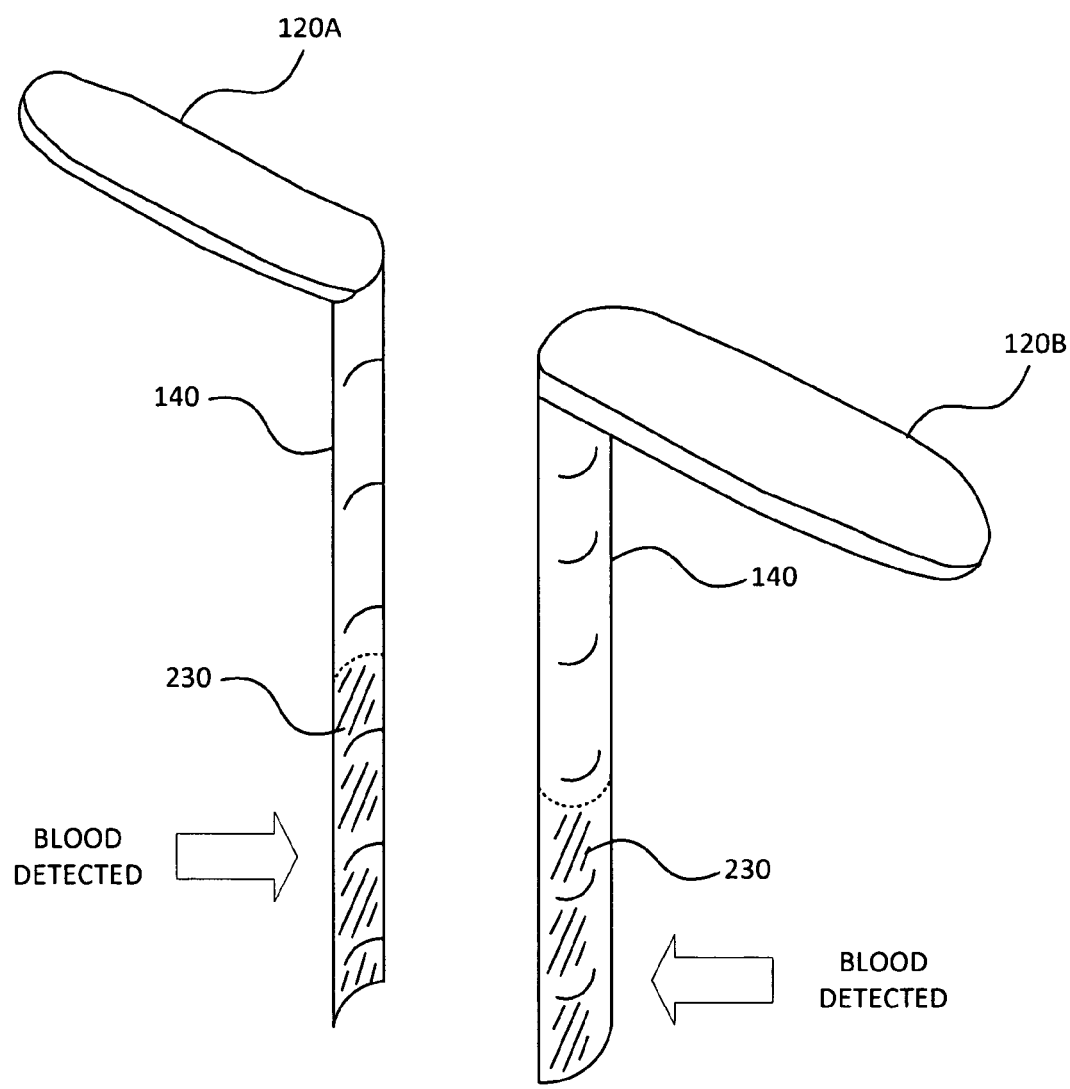

FIGS. 3A-3C illustrate the biopsy needle surrounded by a peel-away sheath in use during a biopsy procedure, according to an example embodiment of the present disclosure.

Referring to FIGS. 3A-3C, the stages of a brain biopsy procedure using the biopsy needle system 100 of the present disclosure, including the peel-away sheath 140, is described herein. With respect to FIG. 3A, the biopsy needle system 100, according to an example embodiment, may be inserted into the brain tissue 200 of a subject with a tumor growth 210 existing within the brain tissue. The purpose of inserting the biopsy needle system 100 into the subject's brain tissue 200 is to extract tissue of the tumor growth 210 for further processing and analysis.

However, as described above in the present disclosure, the insertion of the biopsy needle system 100 into the subject's brain tissue 200 may cause blood to pool, thereby causing a hematoma in the brain of the subject. The existence of hematoma in the subject's brain may be life threatening, and thus, the biopsy needle system 100 may be used to immediately determine the existence of hematoma in the brain so that the appropriate procedures for addressing the hematoma may be performed immediately.

With respect to FIG. 3B, once the biopsy needle system 100 is inserted into the brain tissue 200 (passing the skin of the head 220), but before performing aspiration using the syringe 110 of the biopsy needle system 100, the user (e.g., the surgeon) may grab both the left grip fingerhold 120a and the right grip fingerhold 120b (with left and right hands, respectively, for example), and pull the left grip fingerhold 120a and the right grip fingerhold 120b away from each other. For example, FIG. 3B illustrates that the left grip fingerhold 120a is pulled in the left direction, indicated by the left arrow, and the right grip fingerhold 120b is pulled in the right direction, indicated by the right arrow. The surgeon may simultaneously pull apart the left and right grip fingerholds.

As the surgeon pulls the left grip fingerhold 120a and the right grip fingerhold 120b away from each other, the chemically-impregnated plastic film of the peel-away sheath 140 will tear along the perforations 150, thereby allowing the surgeon to fully remove the peel-away sheath 140 from the biopsy needle system 100. That is, since the peel-away sheath 140 has made contact with the brain tissue during the insertion of the biopsy needle system 100, the surgeon may extract or remove the peel-away sheath 140 in order to determine whether or not hematoma has been detected.

With respect to FIG. 3C, the extracted or removed left and right half of the peel-away sheath 140 is illustrated.

According to example embodiments, once the peel-away sheath 140 has been extracted or removed, the surgeon may view the extracted peel-away sheath 140 to determine whether the plastic film having a testing reagent of the peel-away sheath 140 has come into contact with blood. For example, the testing reagent of the peel-away sheath 140 may provide a visual signal or indication to the surgeon of blood detection by changing to a predetermined color. Depending on example embodiments, for example, the areas where the plastic film of the peel-away sheath 140 has made contact with blood may change color, as shown by the blood detection region 230 of FIG. 3C. Where the plastic film of the peel-away sheath 140 has not made contact with blood, the plastic film will not provide a visual signal, i.e., the color will not change.

As a result of the detection of blood prior to performing aspiration using the biopsy needle system 100, the surgeon is enabled to accurately and timely determine whether hematoma exists in the brain of the subject. Thus, the surgeon may immediately perform procedures suited to address the hematoma, thereby effectively preventing a life threatening condition in the subject. If no hematoma is detected after the peel-away sheath 140 has been extracted or removed, then the surgeon may continue with the brain biopsy procedure by performing aspiration of a piece of tumor tissue 210.

Figure 4:
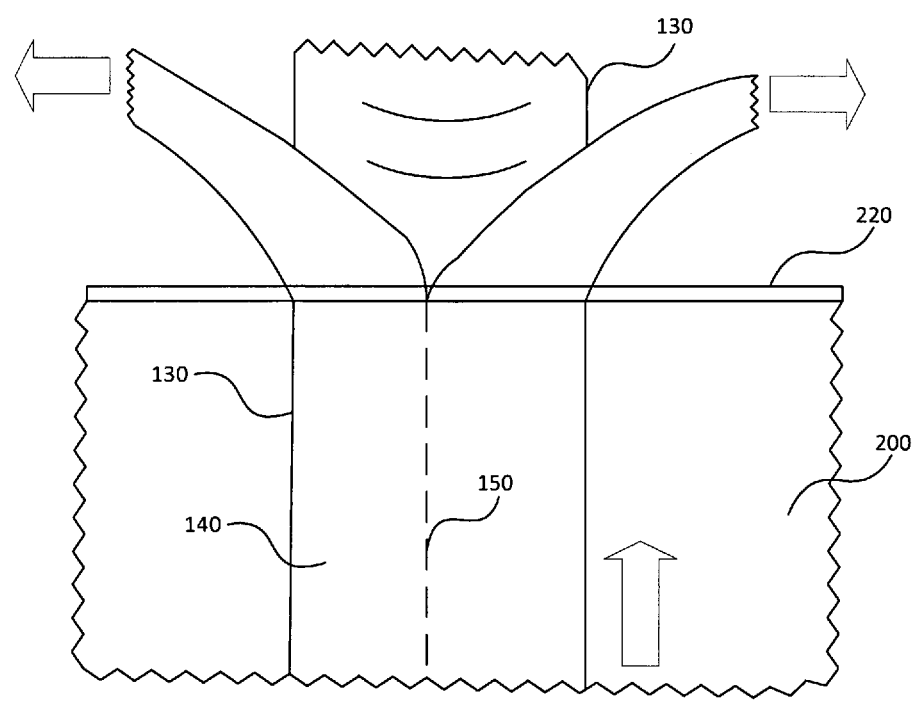
FIG. 4 illustrates a closer view of the peel-away sheath being pulled apart at each of the left and right grip fingerholds.

FIG. 4 illustrates a closer view of the peel-away sheath as it is pulled apart at each of the left and right grip fingerholds. For example, during a procedure of inserting an intracranial probe, the surgeon may insert the barrel 130 surrounded by the peel-away sheath 140 into the brain of the subject. Next, the surgeon may pull the left grip fingerhold 120a in a left direction, for example, and may simultaneously pull the right grip fingerhold 120b in a right direction, for example (as indicated by the left and right arrows of FIG. 4). Upon pulling the left and right grip fingerholds apart from each other, the peel-away sheath 140 may tear at the location of the perforations 150. The perforations 150 are imprinted into the plastic film of the peel-away sheath 140 down the entire length of the peel-away sheath 140. As the left and right grip fingerholds are pulled away from each other, the peel-away sheath 140 moves up the barrel 130 until the peel-away sheath 140 is completely divided and removed from the brain region of the subject.

Accordingly, a user (e.g., a surgeon) may accurately and timely determine the existence of a blood pooling or hematoma when passing an implantable (e.g., deep brain stimulation probes) or non-implantable (e.g., biopsy needle) device into a region of the subject's body to gather tissue for further analysis. In the above disclosure, an exemplary biopsy needle system is provided wherein the needle (e.g., barrel 130) is tightly surrounded by a peel-away sheath that is chemically impregnated with a blood detection composition. The surgeon may insert the biopsy needle into the subject and peel away the chemically impregnated sheath in order to determine whether or not a blood pooling or hematoma exists by viewing a visual signal or indication of blood detection. Further, upon blood detection, the surgeon may act immediately to address the blood pooling or hematoma. Although the above disclosure is mainly directed to a peel away sheath surrounding a biopsy needle, the present disclosure is not limited thereto. That is, the chemically impregnated peel away sheath may tightly surround other devices not described herein.

What is claimed is:

1. An implantation device for brain biopsy needles, the implantation device comprising:

a sheath surrounding a barrel of a brain biopsy needle, the sheath contacting the barrel and having a tubular shape with at least one perforation along an axial direction of the sheath; and at least two grip protrusions attached to an upper portion of the sheath, such that an external force applied to the at least two grip protrusions initiates a tearing of the at least one perforation along the axial direction of the sheath, wherein the sheath comprises a film that is chemically impregnated, such that when the film makes contact with blood, an observable property of the film changes providing an indicator that the blood has been detected, and wherein when the external force is applied to the at least two grip protrusions over a period of time, the at least one perforation along the axial direction of the sheath tears, such that the tubular shape of the sheath is divided.

2. A method for detecting hematoma during a brain biopsy, the method comprising:

providing a chemically-impregnated sheath surrounding a barrel of a brain biopsy needle, the chemically-impregnated sheath having at least two protrusions disposed at an upper portion;

inserting the barrel of the brain biopsy needle together with the chemically-impregnated sheath into the brain;

applying an external force to the at least two protrusions, while the barrel of the brain biopsy needle remains inserted into the brain, such that the external force tears the chemically-impregnated sheath into two portions, separates the chemically-impregnated sheath from the barrel, and extracts the two portions of the sheath from the brain; and providing a blood-detection indicator indicating that the chemically-impregnated sheath detected blood while the chemically-impregnated sheath was inserted into the brain.

\* \* \* \* \*